(12) United States Patent
Breden et al.

(10) Patent No.: US 7,559,945 B2
(45) Date of Patent: Jul. 14, 2009

(54) MULTI-SPECTRAL PHOTON THERAPY DEVICE AND METHODS OF USE

(75) Inventors: Harold Richard Breden, Albuquerque, NM (US); Richard Samuel Murdoch, Albuquerque, NM (US); John Robert Dunning, Santa Fe, NM (US); Thomas M. Lopez, Santa Fe, NM (US)

(73) Assignee: Clarimedix Inc., Boulder, CO (US)

( * ) Notice: Subject to any disclaimer, the term of this patent is extended or adjusted under 35 U.S.C. 154(b) by 385 days.

(21) Appl. No.: 11/331,490

(22) Filed: Jan. 13, 2006

(65) Prior Publication Data
US 2007/0167999 A1    Jul. 19, 2007

(51) Int. Cl.
*A61N 5/06*        (2006.01)
(52) U.S. Cl. .......................................... 607/88; 128/898
(58) Field of Classification Search ............. 607/88–95; 606/3–12; 128/898
See application file for complete search history.

(56) References Cited

U.S. PATENT DOCUMENTS

| | | | |
|---|---|---|---|
| 4,930,504 A * | 6/1990 | Diamantopoulos et al. ..... 607/88 |
| 5,086,788 A | 2/1992 | Castel et al. | |
| 5,218,973 A | 6/1993 | Weaver et al. | |
| 5,358,503 A | 10/1994 | Bertwell et al. | |
| 5,413,550 A | 5/1995 | Castel | |
| 5,464,436 A | 11/1995 | Smith | |
| 5,557,263 A | 9/1996 | Fisher et al. | |
| 5,562,718 A | 10/1996 | Palermo | |
| 5,616,140 A | 4/1997 | Prescott | |
| 5,660,461 A | 8/1997 | Ignatius et al. | |
| 5,683,436 A | 11/1997 | Mendes et al. | |
| 5,743,901 A | 4/1998 | Grove et al. | |
| 5,790,036 A | 8/1998 | Fisher et al. | |
| 5,800,478 A | 9/1998 | Chen et al. | |
| 5,800,479 A | 9/1998 | Thiberg | |
| 5,814,039 A | 9/1998 | Prescott | |
| 5,957,960 A | 9/1999 | Chen et al. | |
| 5,968,034 A | 10/1999 | Fullmer et al. | |
| 5,987,351 A | 11/1999 | Chance | |
| 5,989,245 A | 11/1999 | Prescott | |

(Continued)

OTHER PUBLICATIONS

BIOSCAN, "Biolight 3000 Features and Benefits", no date, 3 pages.

(Continued)

*Primary Examiner*—Ahmed M Farah
(74) *Attorney, Agent, or Firm*—Townsend and Townsend and Crew LLP

(57) ABSTRACT

A multi-spectra photon therapy device and method of use for providing treatment to a subject in need thereof is described. A multi-spectra photon therapy device comprising an array of LEDs having at least two sets of LEDs configured according to a predetermined pattern, with a first set of LEDs emitting light in the about red wavelength and at least a second set of LEDs emitting light in the about infrared wavelength; a frequency generator for modulating a signal to the LED array; and a controller for selecting the frequency applied to the signal and the duration during which the signal is modulated at the selected frequency; a protocol database including a plurality of predetermined sequences of frequencies and durations of time specific to treat or ameliorate predetermined diseases or conditions.

1 Claim, 13 Drawing Sheets

U.S. PATENT DOCUMENTS

| | | | |
|---|---|---|---|
| 5,997,569 A | 12/1999 | Chen et al. | |
| 6,033,431 A | 3/2000 | Segal | |
| 6,045,575 A | 4/2000 | Rosen et al. | |
| 6,063,108 A | 5/2000 | Salansky et al. | |
| 6,084,242 A | 7/2000 | Brown, Jr. | |
| 6,096,066 A | 8/2000 | Chen et al. | |
| 6,135,117 A | 10/2000 | Campbell et al. | |
| 6,156,028 A | 12/2000 | Prescott | |
| 6,157,854 A | 12/2000 | Haber et al. | |
| 6,159,236 A | 12/2000 | Biel | |
| 6,171,331 B1 | 1/2001 | Bagraev et al. | |
| 6,187,029 B1 | 2/2001 | Shapiro et al. | |
| 6,221,095 B1 * | 4/2001 | Van Zuylen et al. | 607/88 |
| 6,238,424 B1 | 5/2001 | Thiberg | |
| 6,238,425 B1 | 5/2001 | Thiberg | |
| 6,249,698 B1 | 6/2001 | Parris | |
| 6,251,127 B1 | 6/2001 | Biel | |
| 6,273,885 B1 | 8/2001 | Koop et al. | |
| 6,306,160 B1 | 10/2001 | Nidetzky | |
| 6,350,275 B1 | 2/2002 | Vreman et al. | |
| 6,413,267 B1 | 7/2002 | Domoulin-White et al. | |
| 6,443,978 B1 | 9/2002 | Zharov | |
| 6,454,791 B1 | 9/2002 | Prescott | |
| 6,456,884 B1 | 9/2002 | Kenney | |
| 6,471,716 B1 | 10/2002 | Pecukonis | |
| 6,494,900 B1 * | 12/2002 | Salansky et al. | 607/89 |
| 6,537,302 B1 | 3/2003 | Thilberg | |
| 6,537,304 B1 | 3/2003 | Oron | |
| 6,596,016 B1 | 7/2003 | Vreman et al. | |
| 6,602,275 B1 | 8/2003 | Sullivan | |
| 6,607,550 B1 * | 8/2003 | Bertwell | 607/88 |
| 6,618,614 B1 | 9/2003 | Chance | |
| 6,641,599 B2 | 11/2003 | Peterson et al. | |
| 6,645,230 B2 | 11/2003 | Whitehurst | |
| 6,663,659 B2 * | 12/2003 | McDaniel | 607/88 |
| 6,669,627 B1 | 12/2003 | Campbell et al. | |
| 6,676,655 B2 | 1/2004 | McDaniel | |
| 6,743,249 B1 | 6/2004 | Alden | |
| D499,491 S | 12/2004 | Kent et al. | |
| D500,141 S | 12/2004 | Kent et al. | |
| 6,860,896 B2 | 3/2005 | Leber et al. | |
| 6,872,221 B2 | 3/2005 | Lytle | |
| D505,728 S | 5/2005 | Kent et al. | |
| 6,887,260 B1 | 5/2005 | McDaniel | |
| 6,896,693 B2 | 5/2005 | Sullivan | |
| D506,009 S | 6/2005 | Kent et al. | |
| 6,918,922 B2 | 7/2005 | Oron | |
| D508,131 S | 8/2005 | Kent et al. | |
| 6,955,684 B2 | 10/2005 | Savage, Jr. et al. | |
| 7,150,710 B2 * | 12/2006 | Haber et al. | 600/9 |
| 2002/0029071 A1 | 3/2002 | Whitehurst | |
| 2002/0198575 A1 | 12/2002 | Sullivan | |
| 2003/0167080 A1 | 9/2003 | Hart et al. | |
| 2004/0044384 A1 | 3/2004 | Leber et al. | |
| 2004/0138726 A1 | 7/2004 | Savage, Jr. et al. | |
| 2004/0158300 A1 | 8/2004 | Gardiner | |
| 2005/0004631 A1 | 1/2005 | Benedict | |
| 2005/0004632 A1 | 1/2005 | Benedict | |
| 2005/0070977 A1 | 3/2005 | Molina | |
| 2005/0137656 A1 | 6/2005 | Malak | |
| 2005/0182460 A1 | 8/2005 | Kent et al. | |
| 2005/0256552 A1 | 11/2005 | White | |
| 2005/0256554 A1 | 11/2005 | Malak | |
| 2006/0282134 A1 * | 12/2006 | Shapiro et al. | 607/88 |
| 2007/0105696 A1 | 5/2007 | Castel et al. | |
| 2007/0156182 A1 | 7/2007 | Castel et al. | |

OTHER PUBLICATIONS

Burke, Thomas, "Nitric Oxide and Its Role in Health and Diabetes," Part 9, no date, 2 pages.

Goldberg, Neil, "Monochromatic Infrared Photo Energy and DPN," Diabetic Microvascular Complications Today, Mar./Apr. 2005, pp. 30-32.

Karu et al. "Exact Action Spectra for Cellular Responses Relevant to Phototherapy," Photomedicine and Laser Surgery, vol. 23, No. 4, pp. 355-361 (2005).

US 6,344,051, 02/2002, Domoulin-White et al. (withdrawn)

* cited by examiner

Protocol Table

| Diagnostic Category | Freq. 1 | Freq. 2 | Freq. 3 | Freq. 4 | Freq. 5 | Freq. 6 | Treatment time | |
|---|---|---|---|---|---|---|---|---|
| Neurological | 146 Hz | 292 Hz | 584 Hz | 4672 Hz | | | 8 | Each frequency will cycle for 1 minute then repeat for the duration of the treatment. |
| Edema | 146 Hz | 584 Hz | 4672 Hz | | | | 10 | Frequencies 2 & 4 will cycle for 2 minutes each then frequency 7 cycles for one minute. They repeat for duration of treatment. |
| Wounds | 146 Hz | 292 Hz | 584 Hz | 292 Hz | 584 Hz | | 4 | Each frequency 1, 2, and 3 will cycle for 1 minute then frequencies 2 and 3 will repeat for the duration of 30 seconds each. |
| Acute Musculoskeletal | 146 Hz | 584 Hz | 1168 Hz | 4672 Hz | | | 8 | Each frequency will cycle for 1 minute then repeat for the duration of the treatment. |
| Chronic Musculoskeletal | 73 Hz | 584 Hz | 1168 Hz | 2336 Hz | 4672 Hz | | 10 | Each frequency will cycle for 1 minute then repeat for the duration of the treatment. |
| Circulatory | 146 Hz | 292 Hz | 584 Hz | | | | 8 | Frequencies 1 & 2 will cycle for 1 minute each then frequency 3 cycles for 2 minutes. They will repeat sequence for duration of treatment. |

FIG. 2

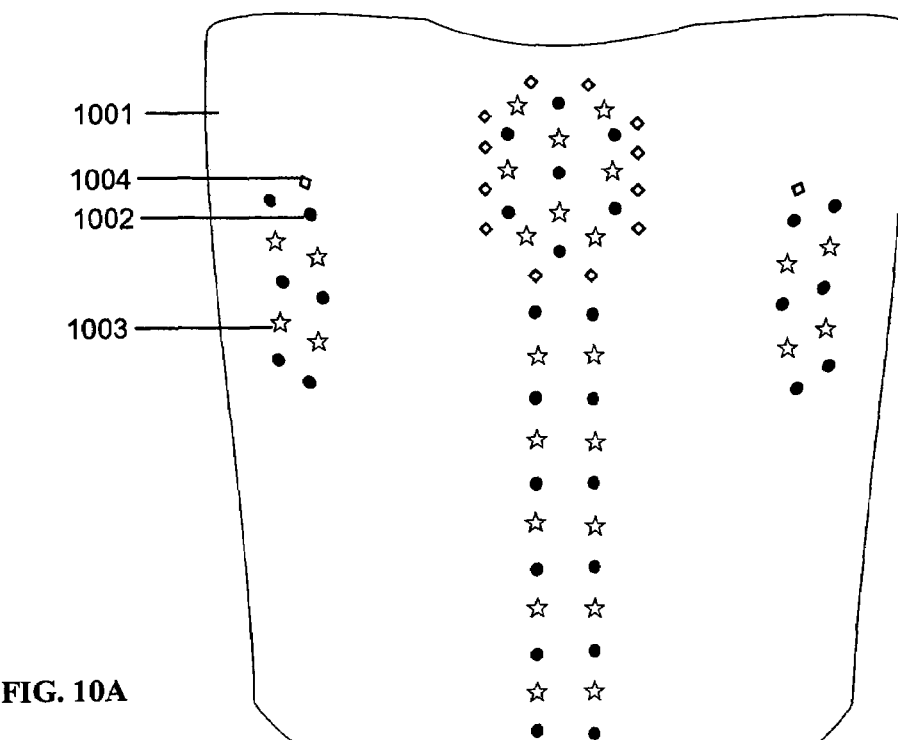
FIG. 10A
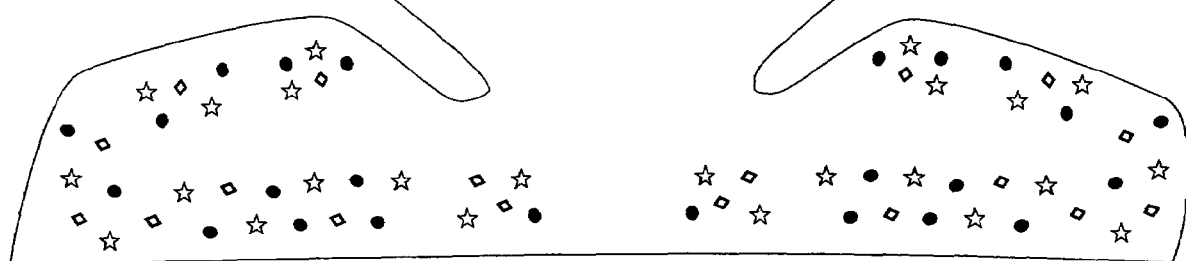
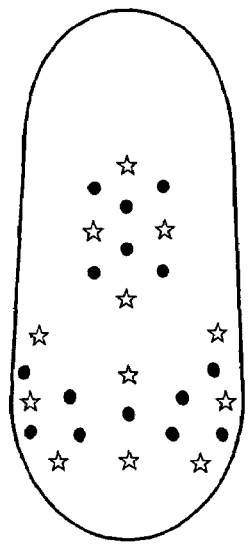
FIG. 10B

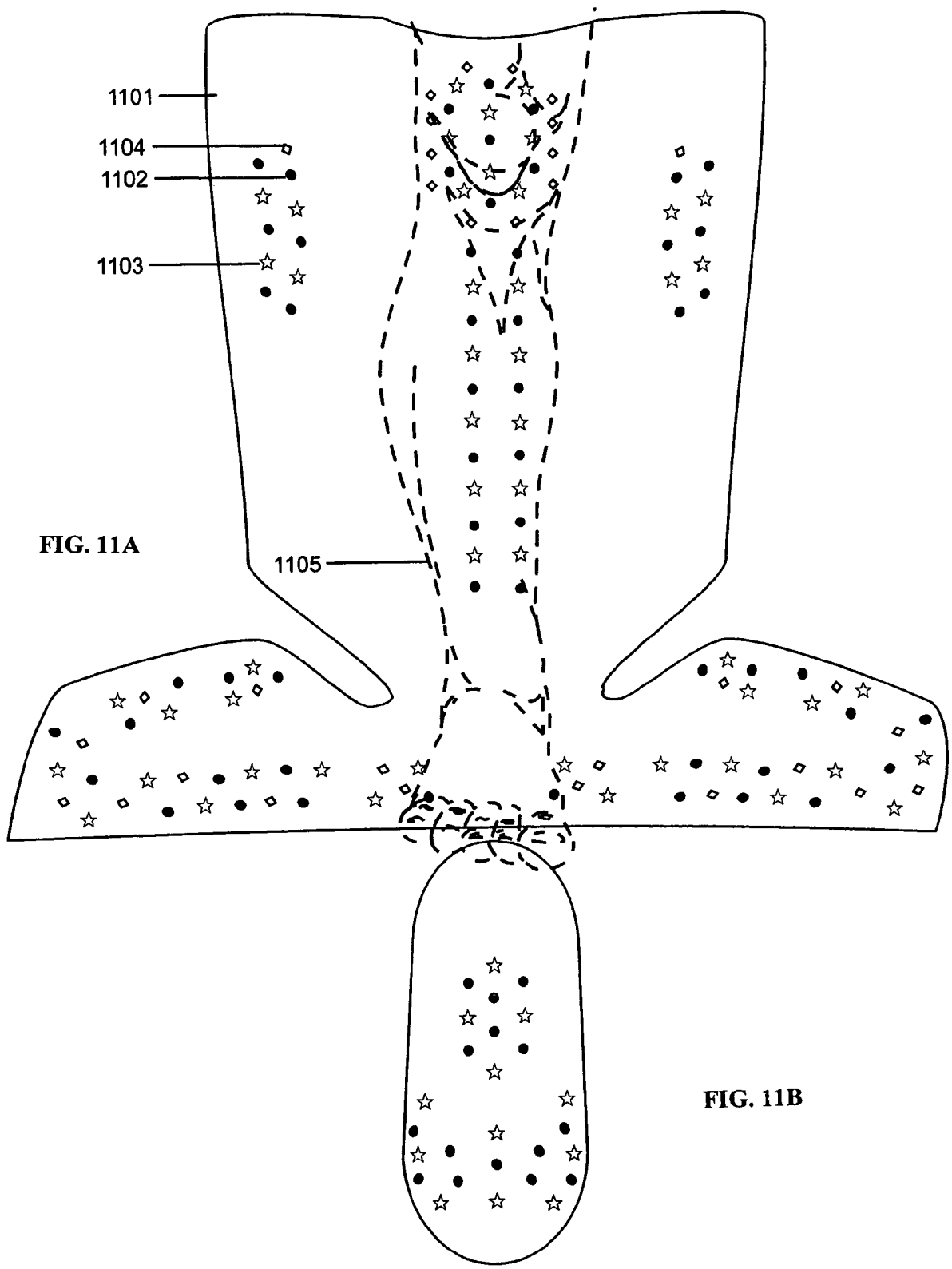

MULTI-SPECTRAL PHOTON THERAPY DEVICE AND METHODS OF USE

BACKGROUND OF THE INVENTION

Photon therapy is the application of light energy to biological tissue for the purpose of stimulating certain biological functions such as natural healing and regrowth processes. Many studies have shown that photon therapy treatment is associated with enhanced healing. Generally, photon therapy is accomplished by radiating light energy into a patient's tissue at or below the skin or surface of the skin. The radiation is applied at wavelengths in the visible range to invisible range by placing the light source in close proximity to the skin.

Photon therapy is based upon the physical properties of electromagnetic waves of light and particles of photons. Photons have certain energies which are proportional to their wavelength. Photons striking matter will cause an electron to be emitted at a rate that is proportional to the kinetic energy of the photon.

BRIEF SUMMARY OF THE INVENTION

A multi-spectra photon therapy device and method of use are provided. A multi-spectra photon therapy device according to a first aspect of the present invention comprises a light emitting diode (LED) array, a frequency generator for modulating a signal to the LED array, a control module for controlling the signal, and a protocol database.

In one embodiment, the LED array comprises at least two sets of LEDs configured according to a predetermined pattern, with a first set of LEDs emitting light in the about red wavelength, and at least a second set of LEDs emitting light in the about infrared wavelength. The LED signal is modulated at two or more frequencies in sequence between about 0.5 and about 10000 Hz, each for a predetermined duration of time. Further, the protocol database includes a plurality of predetermined sequences of frequencies and durations of time specific to treat or ameliorate predetermined diseases or conditions to thereby provide therapeutic treatment regimens corresponding to the predetermined diseases or conditions.

Another aspect of the present invention provides a method of treating a body in need thereof with a multi-spectra photon therapy device. The methods comprise positions a multi-spectra photon therapy device on or near a subject in need of treatment, and illuminating the treatment site with the device in accordance with a treatment protocol.

Other features and aspects of the invention will be apparent from the following detailed description, and from the claims.

BRIEF DESCRIPTION OF THE DRAWINGS

FIG. 2 illustrates a table indicating exemplary frequencies, sequences, and durations useful to treat or ameliorate exemplary diagnostic categories.

FIGS. 10A and 10B illustrates a multi-spectra photon therapy lower extremity liner for use with a boot device wherein the LED array pattern is reflective of anatomical points of interest in the foot, ankle and lower leg according to one embodiment of the present invention.

FIGS. 11A and 11B illustrates the multi-spectra photon therapy lower extremity liner for use with a boot device with a body lower extremity placed near the liner, according to one embodiment of the present invention.

DETAILED DESCRIPTION OF THE INVENTION

Figure 1:
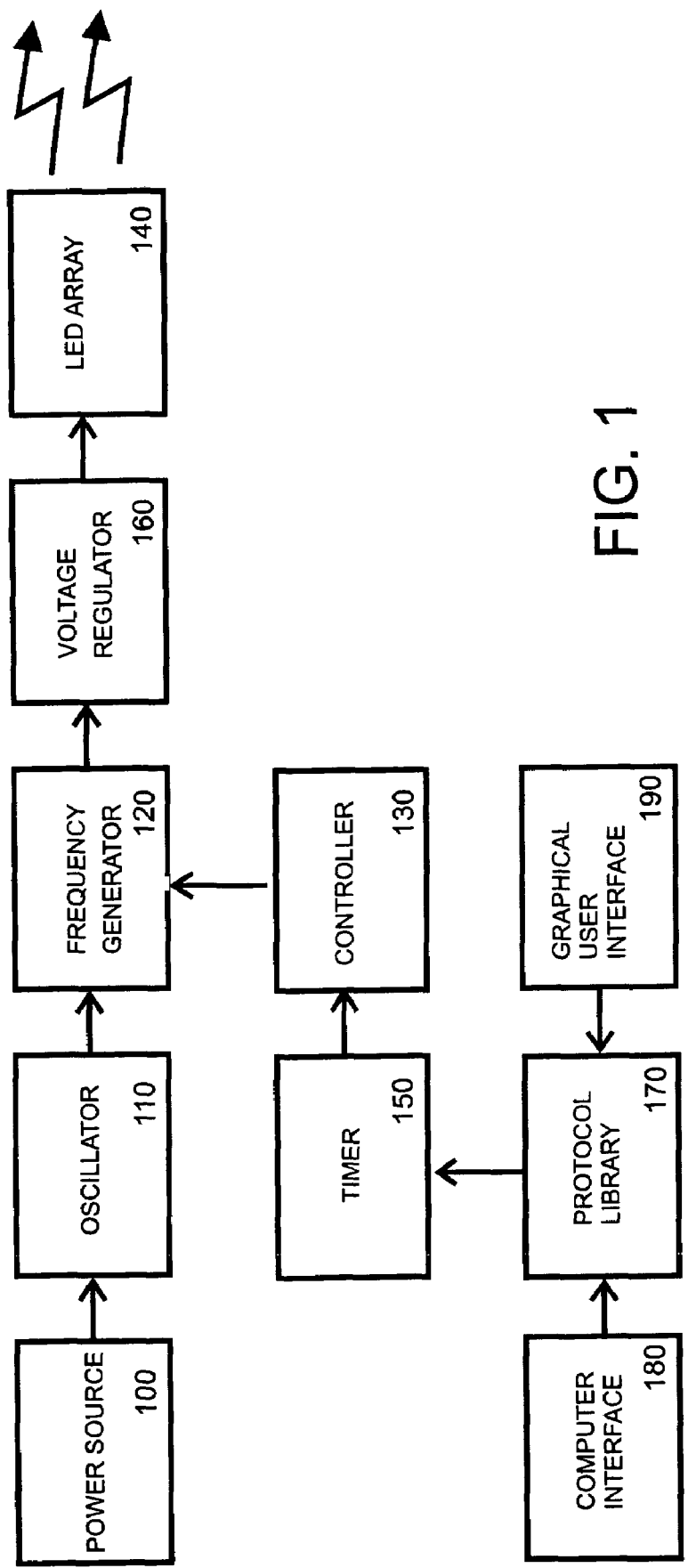
FIG. 1 illustrates a block diagram according to one embodiment of the present invention.

The present invention generally relates to devices and methods for multi-spectra photon (MSP) therapy. The devices and methods of the invention involve the use of arrays of light emitting diodes (LEDs) comprising at least two sets of LEDs which emit light at differing wavelengths. The sets of LEDs are configured within the array in predetermined patterns, and are activated at two or more frequencies in sequence for predetermined durations of time.

Without intending to be limited by theory, MSP synergistically combines specifically designed placement of LED arrays, wavelength selection, illumination intensity, and pulsation of photon sources to treat diseases and conditions associated with nerve and/or soft tissue damage, e.g., caused by diabetic peripheral neuropathy (DPN). In certain aspects of the invention, treatments are provided involving inserting the leg and/or foot into a MSP device, adjusting for comfort, and activating the device for a pre-programmed treatment of approximately 5-45 minutes.

MSP therapy uses photon sources of specific wavelengths pulsed at predetermined intervals, which when placed in a predetermined pattern at regular validated sites (i.e., anatomical locations). Again, without intending to be limited by theory, use of MSP therapy in such a manner is believed to aid in improving circulation while reducing the pain associated with DPN. Further, it is believed that the application of various wavelengths at specific pulsations have a stimulating effect on the synthesis of RNA and DNA. The specific wavelengths also initiate a series of events that result in enhanced metabolic activity in the irradiated tissues, which can lead to tissue and nerve repair over a course of treatments. In accordance with the present invention, it has been found that specific sequences of pulsations of the LED arrays, for specific durations of time can improve cellular response to the MSP therapy.

More particularly, photons of certain wavelengths can penetrate the skin to various depths depending on the energy of the photon. Visible light is composed of photons in the energy range of around 2 to 3 eV which triggers the photo receptors in the eye. The quantum energy of infrared photons is in the range of about 0.001 to 1.7 eV which is in the range of energies separating the quantum states of molecular vibrations. The result of infrared absorption is heating of the tissue since it increases molecular vibrational activity. Infrared is absorbed more strongly than microwaves, but less strongly than visible light. Infrared light is in the invisible spectrum above red from about 700 nm to 2000 nm and penetrates the skin to the subcutaneous blood vessels and has been used for photographic imaging of the same. Red light is in the visible spectrum from about 600 nm to 700 nm. Visible red light, at a wavelength of 660 nm (nanometers), penetrates human tissue to a depth of, e.g., about 8-10 mm. Skin layers, because of their high blood and water content, absorb red light very readily. It is very beneficial in treating problems close to the surface such as wounds, cuts, scars, trigger points, and acupuncture points, and is particularly effective in treating infections. Infrared light at 950 nm penetrates to a depth of, e.g., about 30-40 mm and up to about 20-25 cm, which makes it more effective for bones, joints, and deep muscles.

In one aspect of the invention, referring to FIG. 1, a multi-spectra photon therapy device is illustrated. A frequency generator 120 modulates a signal produced by oscillator 110. The modulated signal is provided to the LED array 140 whereupon the LED array 140 emits light. A timer 150 controls the on/off duration of the controller 130. The controller controls the duration of the treatment cycle in general. More specifically, the controller 130 controls the specific frequencies generated by the frequency generator, the order in which the frequencies are applied to the signal and the length of time each frequency is applied to the signal going to the LEDs. In certain embodiments, the controller may interface with a protocol list in the protocol database 170. The protocol database may be a dynamic library that is optionally connected to a computer interface 180 allowing for the addition of new protocols as they are needed or developed. An optional graphical user interface (GUI) 190 may interface with the protocol library 170 or the computer interface 180 to facilitates the operation and selection of the protocols that are stored in the protocol database 170. A power source 100 provides power to the LED array. A voltage regulator 160 regulates voltage in the device. In an alternative embodiment, a multi-spectra photon therapy device comprises an oscillator 110, a frequency generator 120, an LED array 140, a timer 150 and a controller 130.

According to another embodiment of the present invention, an arrangement of LEDs are contained within a housing. The light emitted from the LEDs is visible through a transparent window positioned on at least a portion of one wall of the housing. The housing for the LEDs is connected to the circuitry of the controlling device described in FIG. 1 via a connector. In yet another embodiment, the LEDs are located outside of the housing. For example the LEDs are embedded within a suitable material such as neoprene and connected to the circuitry of the controlling device described in FIG. 1 via a connector. The position of the LEDs in a material such as neoprene permits the multi-spectra photon therapy device to wrap around a portion of the body or otherwise anatomically conform to the portion of the body in need of treatment.

According to yet another embodiment of the invention, the LEDs are arranged in a predetermined configuration wherein the configuration may be ordered, such as a linear configuration, or positioned according to anatomical points of interest, such as, but not limited to, acupuncture meridians, neuropathy points, acupressure points, trigger points, nerve bundles, key neurovascular bundles, tissues types of interest, or other anatomical structures of interests for a particular location of the body. Alternatively, the LEDs may be arranged in a random pattern.

According to one embodiment of the present invention, the LEDs are composed of a first wavelength group. For example, the first wavelength group may be in the about red wavelengths (by way of non-limiting example, about 0.600 to about 0.700 μm, or about 0.620 to about 0.700 μm wavelength). In yet another embodiment of the present invention, the LEDs are composed of a second wavelength group. For example the second wavelength group may be in the about infrared wavelengths, e.g., the near infrared wavelengths (by way of non-limiting example, in the about 0.700 to about 1.400 μm wavelength, more particularly, 740 nm to about 905 nm). In other embodiments, the LEDs are composed of a third, forth, and/or fifth wavelength group. For example, the third wavelength group may be in the about infrared wavelength (including near infrared) or the about blue wavelengths. In other embodiments, the LEDs may range from about 100 nm to about 1500 nm, from about 100 nm to about 1200 nm, or from about 400 nm to about 880 nm. In certain embodiments of the present invention, the LEDs are a combination of a first wavelength group and a second wavelength group, which emit light in, e.g., about red and about infrared wavelengths. In other embodiments, the LED array may comprise a third, forth, and/or fifth set of LEDs which emit light in, e.g., about near infrared, about blue, about UV, etc. wavelengths.

In certain embodiments, the LED arrays include at least three sets of LEDs, with a first set of LEDs emitting light in the about red wavelengths, a second set of LEDs emitting light in the about infrared wavelengths, and a third set of LEDs emitting light in the about infrared wavelengths. In certain preferred embodiments, the first set of LEDs may emit light at, e.g., about 630 to about 660 nm, the second set of LEDs may emit light at, e.g., about 740 to about 760 nm, and the third set of LEDs may emit light at, e.g., about 880 to about 905 nm.

A frequency sequence and/or timing sequence of the first set of LEDs may be varied in relation to the second set of LEDs, depending on the intended therapeutic use of the device. In certain embodiments, the signal powering the LEDs may be cycled through multiple frequencies over a predetermined period of time. Alternatively, the signal may remain at a single frequency. For example, the frequency may changed according to an ordered sequence, or may be changed at random for frequencies in the frequency range from about 0.5 Hz to about 10000 Hz, each for a predetermined amount of time (e.g., about 1 second to about 30 minute).

Example frequencies include: about 0.5 Hz, about 1.2 Hz, about 2.5 Hz, about 3.0 Hz, about 3.5 Hz, about 3.9 Hz, about 4.9 Hz, about 5.8 Hz, about 6.0 Hz, about 6.8 Hz, about 7.0 Hz, about 7.8 Hz, about 9.2 Hz, about 9.4 Hz, about 9.6 Hz, about 12 Hz, about 20 Hz, about 64 Hz about 72 Hz, about 96 Hz, about 104 Hz, about 112 Hz, about 120 Hz, about 128 Hz, about 144 Hz, about 146 Hz, about 192 Hz, about 248 Hz, about 292 Hz, about 300 Hz, about 304 Hz, about 328 Hz, about 408 Hz, about 421 Hz, about 423 Hz, about 424 Hz, about 425 Hz, about 427 Hz, about 432 Hz, about 434 Hz, about 440 Hz, about 464 Hz, about 500 Hz, about 520 Hz, about 584 Hz, about 600 Hz, about 624 Hz, about 648 Hz, about 660 Hz, about 662 Hz, about 664 Hz, about 676 Hz, about 712 Hz, about 728 Hz, about 728 Hz, about 760 Hz, about 764 Hz, about 776 Hz, about 784 Hz, about 785 Hz, about 800 Hz, about 803 Hz, about 804 Hz, about 807 Hz, about 818 Hz, about 823 Hz, about 829 Hz, about 830 Hz, about 832 Hz, about 861 Hz, about 864 Hz, about 873 Hz, about 877 Hz, about 880 Hz, about 1168 Hz, about 2128 Hz, about 2180 Hz, about 2182 Hz, about 2336 Hz, about 2720 Hz, about 3000 Hz, about 3120 Hz, about 4500 Hz, about 4672 Hz, and about 10000 Hz.

Example frequency sequences include: (a) about 146 Hz, about 292 Hz, about 584 Hz, and about 4672 Hz, each for about 1 second to about 5 minute; (b) about 146 Hz, about 292 Hz, and about 4672 Hz, each for about 1 second to about 5 minute; (c) about 146 Hz, about 584 Hz, and about 4672 Hz, each for about 1 second to about 5 minute; (d) about 146 Hz, about 292 Hz, about 584 Hz, about 292 Hz, and about 584 Hz, each for about 1 second to about 5 minute; (e) about 146 Hz, about 584 Hz, about 1168 Hz, and about 4672 Hz, each for about 1 second to about 5 minute; (f) about 73 Hz, about 584 Hz, about 1168, about 2336 Hz, and about 4672, each for about 1 second to about 5 minute; (g) about 146 Hz, about 292 Hz, and about 584 Hz, each for about 1 second to about 5 minute; (h) about 292 Hz, about 146 Hz, and about 4672 Hz, each for about 1 second to about 5 minute; (i) about 4672 Hz, about 146 Hz, about 292 Hz, about 584 Hz, and about 4672 Hz, each for about 1 second to about 5 minute; (j) about 292 Hz, about 146 Hz, and about 584 Hz, each for about 1 second to about 5 minute; and (k) combinations thereof. Again, each frequency may be energized for an amount of time independently selected from about 1 second to about 5 minutes, e.g., each for about 30 seconds, 1 minute, 2 minutes, 3 minutes, 4 minutes, or 5 minutes, independently selected for each frequency.

In certain embodiments of the invention, the first set of LEDs may be activated concurrently with the second set of LEDs, or alternatively may be activated in alteration with the second set of LEDs. Further, in some embodiments, it is preferably that the LEDs are activated such that at least one set of LEDs are illuminated at any given point in time during the treatment cycle, i.e., that the LEDs are activated so as to provide substantially continuous illumination by at least one set of LEDs at all times during the treatment cycle. In such embodiments, there will be no substantial "dark periods" where no LEDs are illuminated between frequency sequences.

Referring now to FIG. 2, a series of predefined sequences of frequencies with duration of application of each frequency suitable for exemplary diagnostic categories defining a treatment protocol are illustrated. In certain embodiments, each treatment protocol may be individually selectable through the use of the graphical user interface, control unit dial, number pad, etc. In certain embodiments, the treatment protocols may preferably deliver between about 1 to about 1,000 joules, from about 1 to about 100 joules, from about 4 to about 20 joules, or from about 4 and about 12 joules of energy to the treatment area during the treatment time. Any LED of suitable wavelength, power output, and viewing angle may be used. By way of non-limiting example, in certain embodiments, the LED array may comprise 40 milliwatt LEDs of varying predetermined wavelengths.

Figure 3:
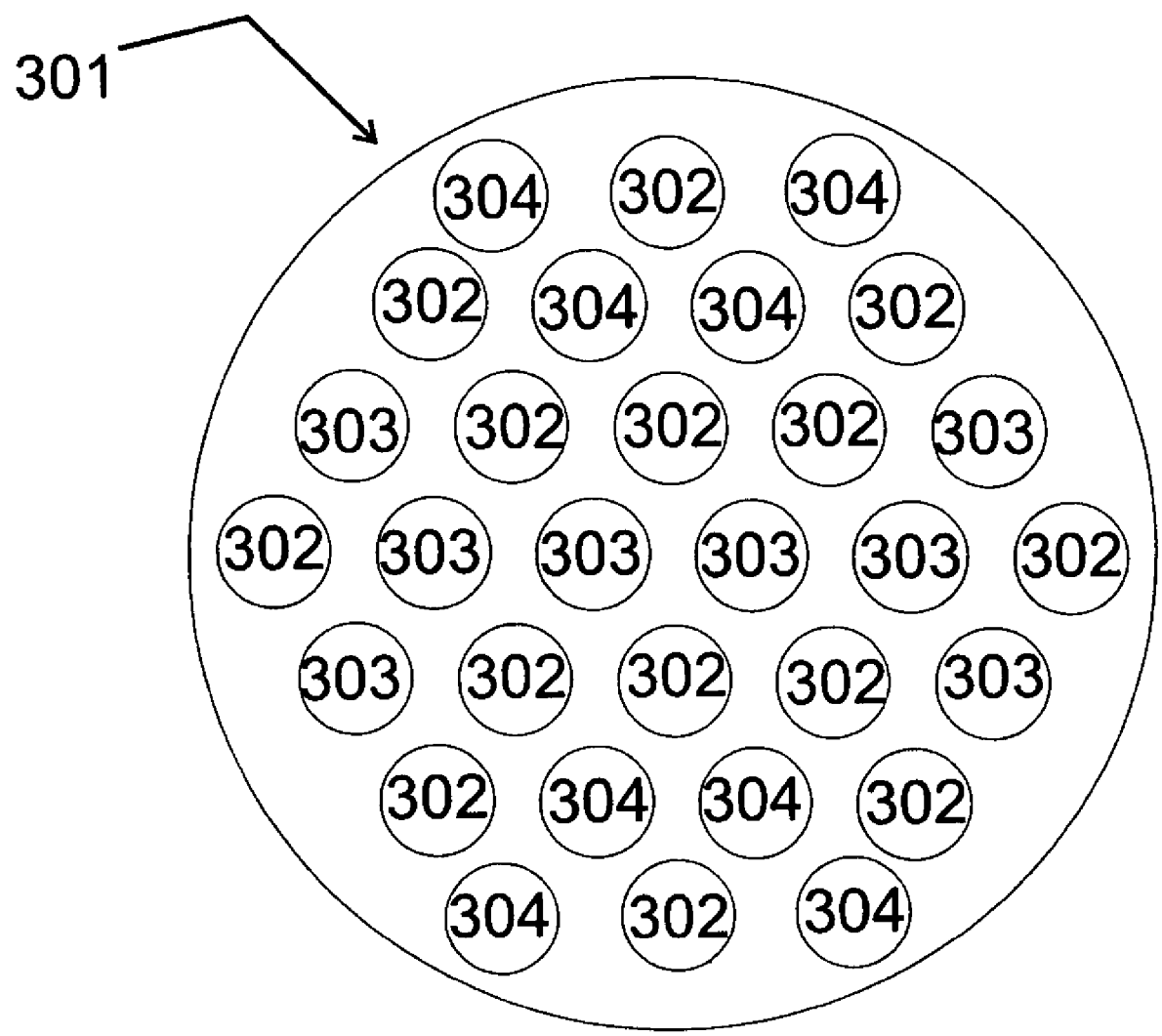
FIG. 3. illustrates a LED array pattern according to one embodiment of the present invention.

According to another embodiment of the present invention, the configuration of the LEDs is varied in a manner that promotes the general health of a person in need thereof. Referring now to FIG. 3, an exemplary LED array is configured on a cluster head 301 having multiple rows of lights (for example 7 rows) wherein the cluster head, which may be shaped, e.g., as a disk or a pad (not shown), may be of any size, preferably about 20-50 mm in diameter. The LED array may include a first set of LEDs 302 interspersed with at least a second set of LEDs 303. In certain embodiments, the LED array may also include a third set of LEDs, 304 interspersed with the first and second set. In certain embodiments, the first set of LEDs 302 may emit light in the about red wavelengths, e.g., about 630 nm, the second set of LEDs 303 may emit light in the about infrared wavelengths, e.g., about 760 nm, and the third set of LEDs 304 may emit light in the about infrared wavelengths, e.g., about 880 nm. Other combinations of LEDs are also possible, as described herein.

The frequency applied to the signal may be varied during a treatment session. The treatment sessions can be for a predetermined period of time, for example, from about 1 minute to about 45 minutes using a timer, or controlled manually. According to one embodiment of the present invention, the signal for the LED pattern illustrated in FIG. 3 may be modulated by any of a selection of protocols stored in the protocol database.

Figure 4:
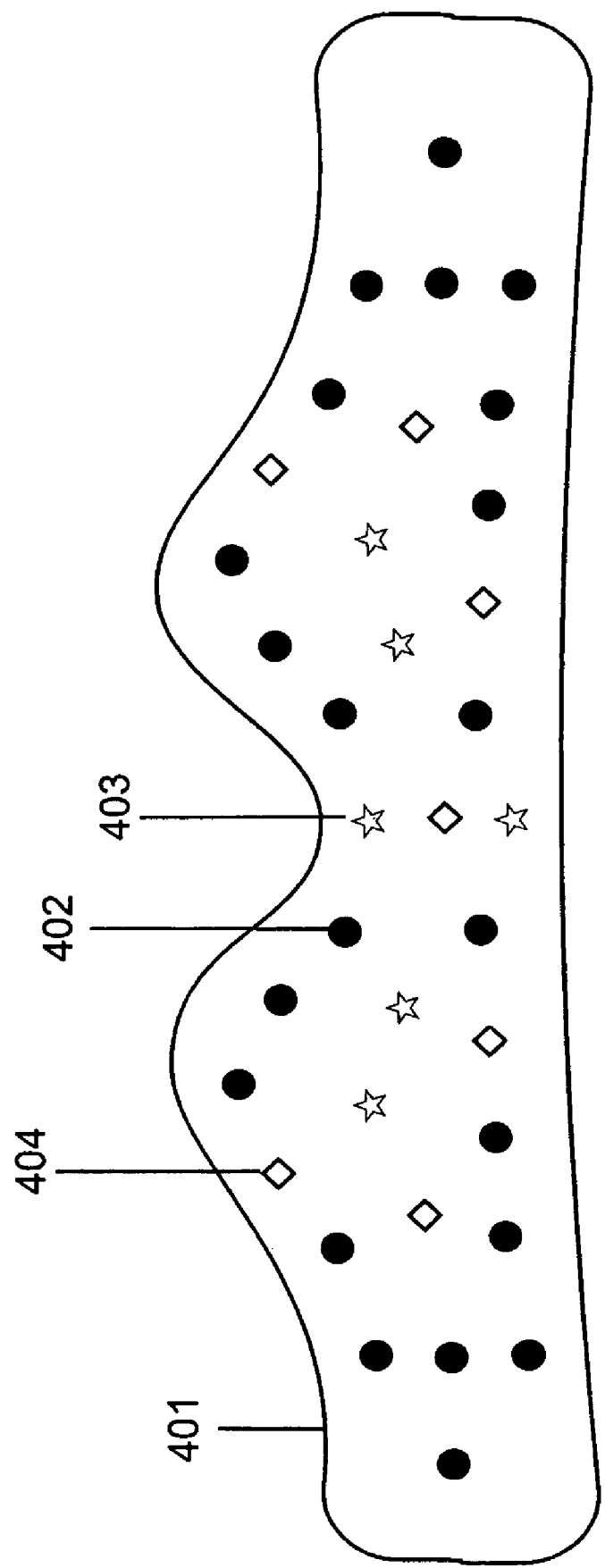
FIG. 4 illustrates a multi-spectra photon therapy pad device displaying a LED array having a pattern reflective of anatomical points of interest in the cervical region according to one embodiment of the present invention.

Referring now to FIG. 4, a multi-spectra photon therapy cervical pad 401 is illustrated according to one embodiment of the present invention. The cervical pad multi-spectra photon therapy device may include a first set of, e.g., red LEDs illustrated as circles (402) interspersed with at least a second set of, e.g., infrared LEDs illustrated as stars (403). positioned through out the cervical pad. In certain embodiments, the cervical pad 401 may also include a third set of, e.g., infrared LEDs illustrated as diamonds (404). In certain embodiments, the first set of LEDs 402 may emit light in the about red wavelengths, e.g., about 630 nm, the second set of LEDs 403 may emit light in the about infrared wavelengths, e.g., about 760 nm, and the third set of LEDs 404 may emit light in the about infrared wavelengths, e.g., about 880 nm. Other combinations of LEDs are also possible, as described herein. Further, in certain embodiments, the LEDs may be configured in the array in a predetermined pattern reflective of anatomical points of interest in the cervical region.

The LEDs of FIG. 4 may be connected to a controller (not shown). The controller may include a timer 150 (FIG. 1.), that controls the on/off duration of the controller, a controller 130 (FIG. 1) that controls the frequency generator 120 (FIG. 1), and an oscillator 110 (FIG. 1) that provides an oscillated signal to the frequency generator 120 (FIG. 1) which provides a modulated signal to the LEDs. A protocol database 170 (FIG. 1) that stores a collection of predetermine frequencies and durations specific to particular conditions or diagnosis. The protocol database 170 (FIG. 1) may optionally be connected to a computer interface 180 (FIG. 1) that allows loading of new protocols as they are needed or developed. The modulated signal is provided to the LED array as illustrated in FIG. 4 whereupon the LED array emits light.

Figure 5:
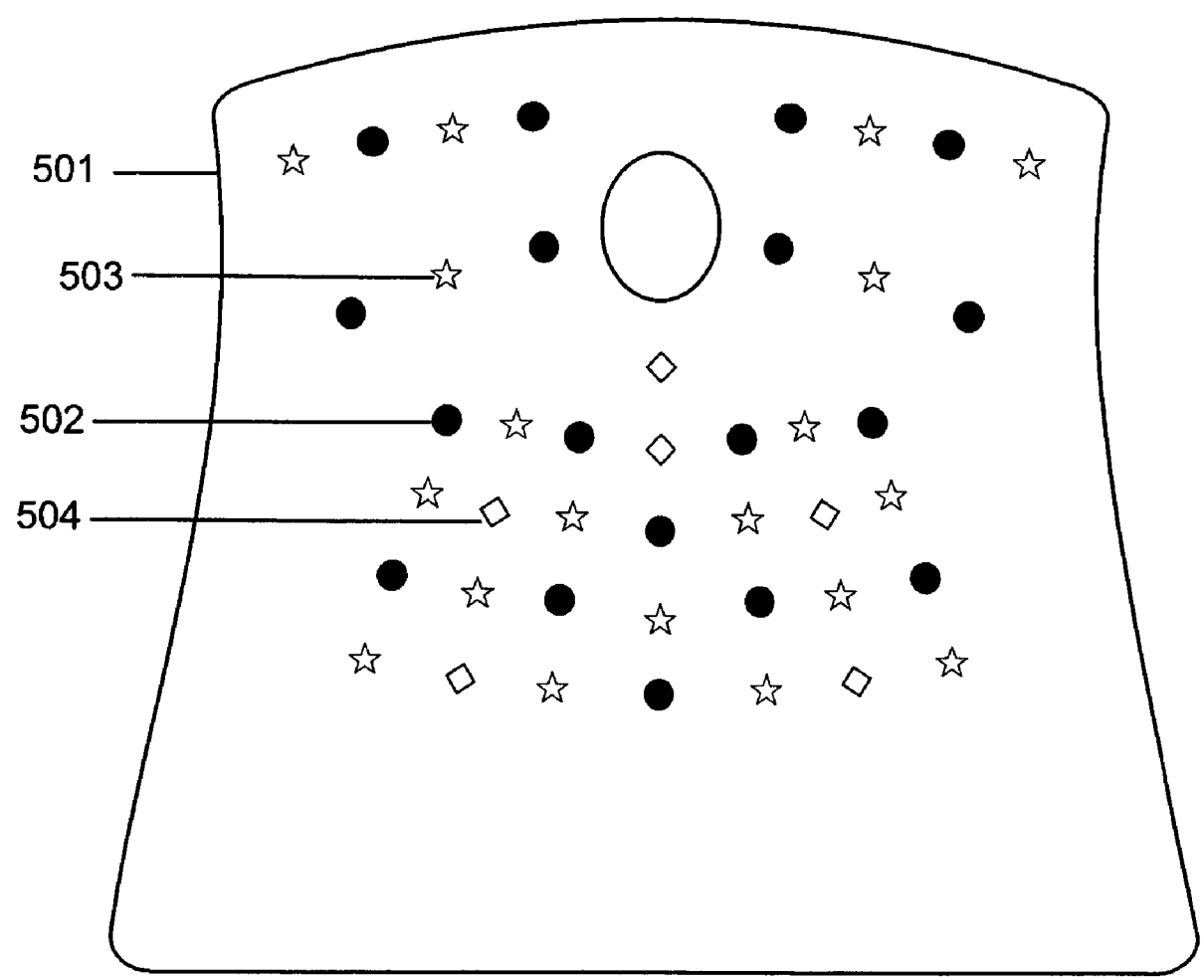
FIG. 5 illustrates a multi-spectra photon therapy pad device displaying a LED array pattern reflective of anatomical points of interest in the wrist according to one embodiment of the present invention.

Referring now to FIG. 5, a multi-spectra photon therapy wrist pad 501 is illustrated according to one embodiment of the present invention. The wrist pad multi-spectra photon therapy device may include a first set of, e.g., red LEDs illustrated as circles (502) interspersed with at least a second set of, e.g., infrared LEDs illustrated as stars (503) positioned through out the wrist pad. In certain embodiments, the wrist pad may also include a third set of, e.g., infrared LEDs illustrated as diamonds (504). Again, in certain embodiments, the first set of LEDs 502 may emit light in the about red wavelengths, e.g., about 630 nm, the second set of LEDs 503 may emit light in the about infrared wavelengths, e.g., about 760 nm, and the third set of LEDs 504 may emit light in the about infrared wavelengths, e.g., about 880 nm. Other combinations of LEDs are also possible, as described herein. Further, in certain embodiments, the LEDs may be configured in the array in a predetermined pattern reflective of anatomical points of interest in the wrist.

The LEDs of FIG. 5 may be connected to a controller (not shown). The controller may include a timer 150 (FIG. 1.), that controls the on/off duration of the controller, a controller 130 (FIG. 1) that controls the frequency generator 120 (FIG. 1), and an oscillator 110 (FIG. 1) that provides an oscillated signal to the frequency generator 120 (FIG. 1) which provides a modulated signal to the LEDs. A protocol database 170 (FIG. 1) that stores a collection of predetermine frequencies and durations specific to particular conditions or diagnosis. The protocol database 170 (FIG. 1) may optionally be connected to a computer interface 180 (FIG. 1) that allows loading of new protocols as they are needed or developed. The modulated signal is provided to the LED array as illustrated in FIG. 5 whereupon the LED array emits light.

Figure 6:
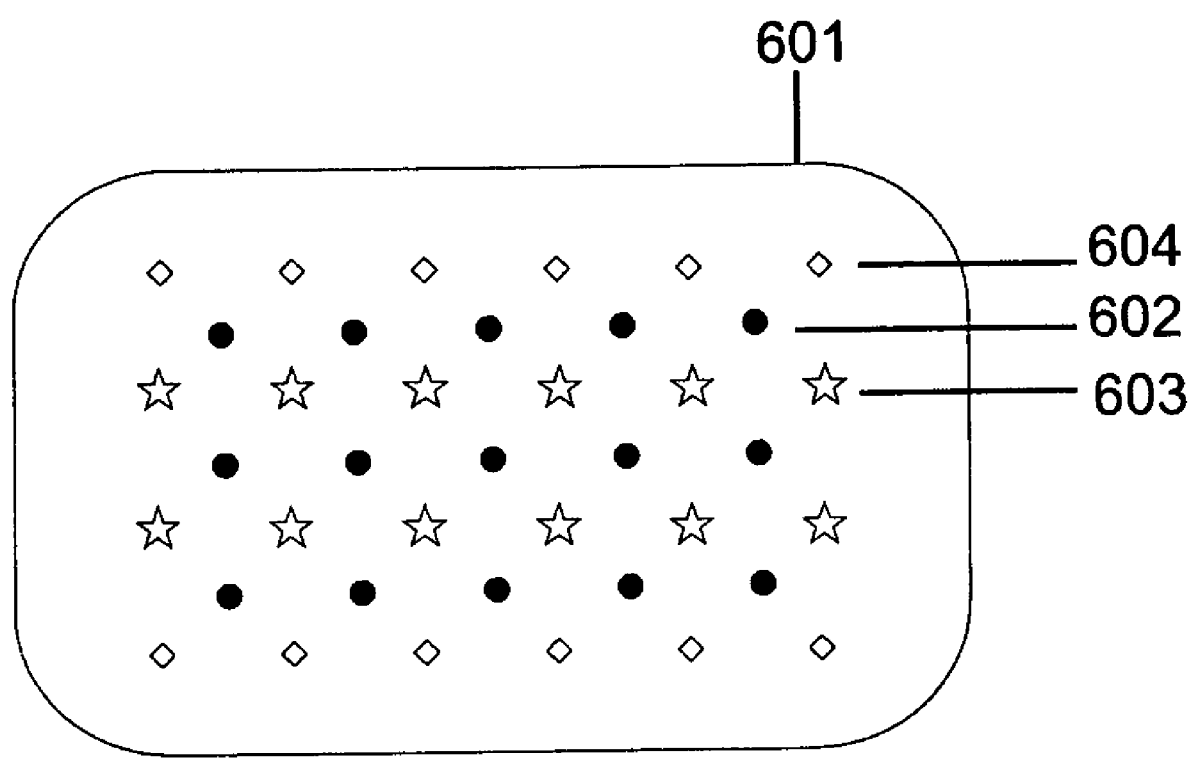
FIG. 6 illustrates a multi-spectra photon therapy pad device displaying a LED array having a random pattern according to one embodiment of the present invention.

Referring now to FIG. 6, a multi-spectra photon therapy light patch 601 is illustrated according to one embodiment of the present invention. A first set of, e.g., red LEDs 602 are located, e.g., in rows 2, 4, and 6. At least a second set of, e.g., infrared LEDs 603 are located, e.g., in rows 3 and 5. In certain embodiments, a third set of, e.g., infrared LEDs 604 are located, e.g., in rows 1 and 7. Again, in certain embodiments, the first set of LEDs 602 may emit light in the about red wavelengths, e.g., about 630 nm, the second set of LEDs 603 may emit light in the about infrared wavelengths, e.g., about 760 nm, and the third set of LEDs 604 may emit light in the about infrared wavelengths, e.g., about 880 nm. Other combinations of LEDs are also possible, as described herein.

The LEDs of FIG. 6 may be connected to a controller (not shown). The controller may include a timer 150 (FIG. 1.), that controls the on/off duration of the controller, a controller 130 (FIG. 1) that controls the frequency generator 120 (FIG. 1), and an oscillator 110 (FIG. 1) that provides an oscillated signal to the frequency generator 120 (FIG. 1) which provides a modulated signal to the LEDs. A protocol database 170 (FIG. 1) that stores a collection of predetermine frequencies and durations specific to particular conditions or diagnosis. The protocol database 170 (FIG. 1) may optionally be connected to a computer interface 180 (FIG. 1) that allows loading of new protocols as they are needed or developed. The modulated signal is provided to the LED array as illustrated in FIG. 6 whereupon the LED array emits light.

Figure 7:
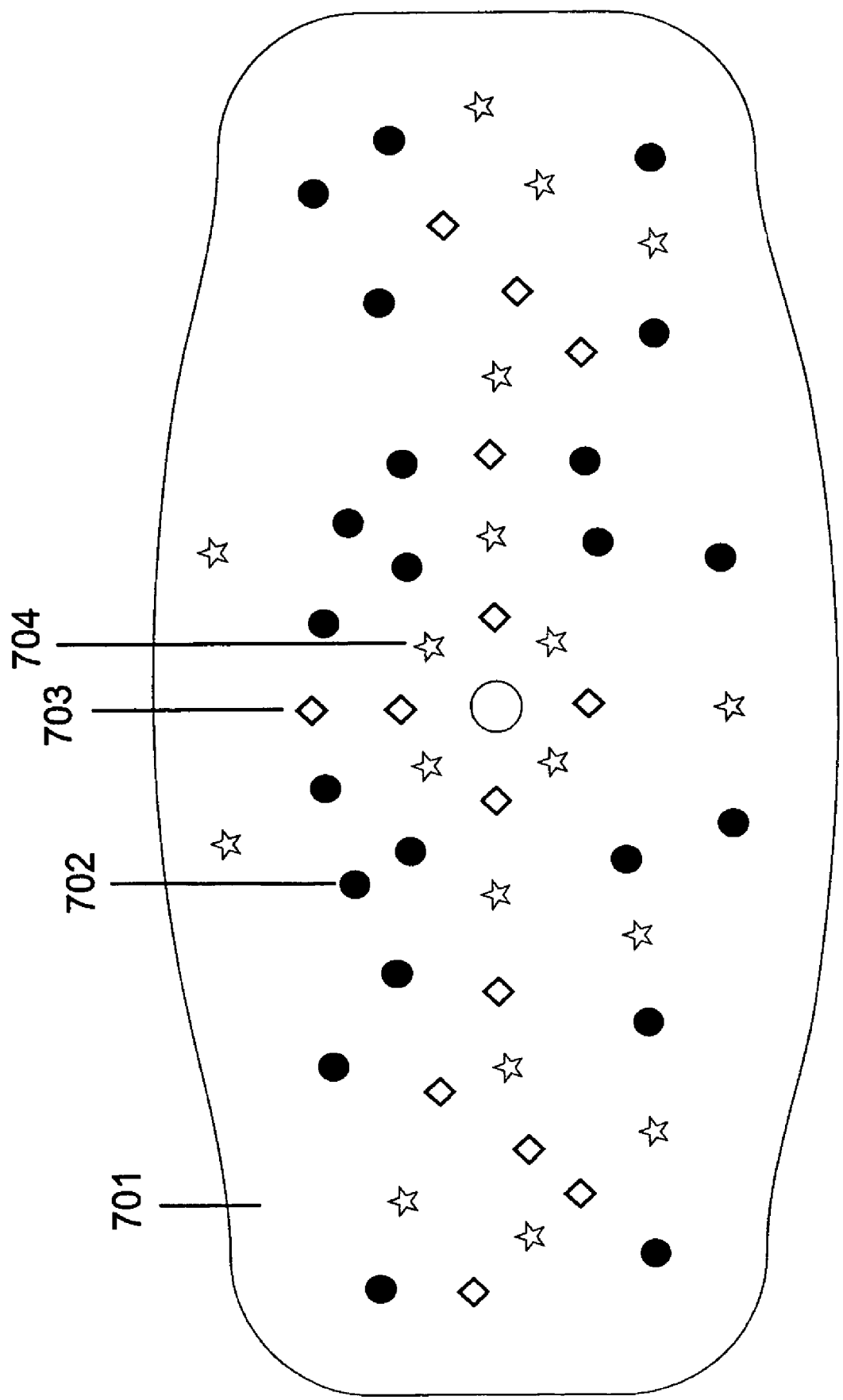
FIG. 7 illustrates a multi-spectra photon therapy pad device wherein the LED array pattern is reflective of anatomical points of interest in the knee according to one embodiment of the present invention.

Referring now to FIG. 7, a multi-spectra photon therapy knee pad is illustrated according to one embodiment of the present invention. The kneepad multi-spectra photon therapy device may include a first set of, e.g., red LEDs illustrated as circles (702) interspersed with at least a second set of, e.g., infrared LEDs illustrated as stars (703) positioned through out the kneepad. In certain embodiments, the kneepad may also include a third set of, e.g., infrared LEDs illustrated as diamonds (704) interspersed throughout the first and second set of LEDs. Again, in certain embodiments, the first set of LEDs 702 may emit light in the about red wavelengths, e.g., about 630 nm, the second set of LEDs 703 may emit light in the about infrared wavelengths, e.g., about 760 nm, and the third set of LEDs 704 may emit light in the about infrared wavelengths, e.g., about 880 nm. Other combinations of LEDs are also possible, as described herein. Further, in certain embodiments, the LEDs may be configured in the array in a predetermined pattern reflective of anatomical points of interest in the knee.

The LEDs of FIG. 7 may be connected to a controller (not shown) through a connector (not shown). The controller contains a timer 150 (FIG. 1.), that controls the on/off duration of the controller, a controller 130 (FIG. 1) that controls the frequency generator 120 (FIG. 1), and an oscillator 110 (FIG. 1) that provides an oscillated signal to the frequency generator 120 (FIG. 1) which provides a modulated signal to the LEDs. A protocol database 170 (FIG. 1) that stores a collection of predetermine frequencies and durations specific to particular conditions or diagnosis. The protocol database 170 (FIG. 1) may optionally be connected to a computer interface 180 (FIG. 1) that allows loading of new protocols as they are needed or developed. The modulated signal is provided to the LED array as illustrated in FIG. 7 whereupon the LED array emits light.

Figure 8:
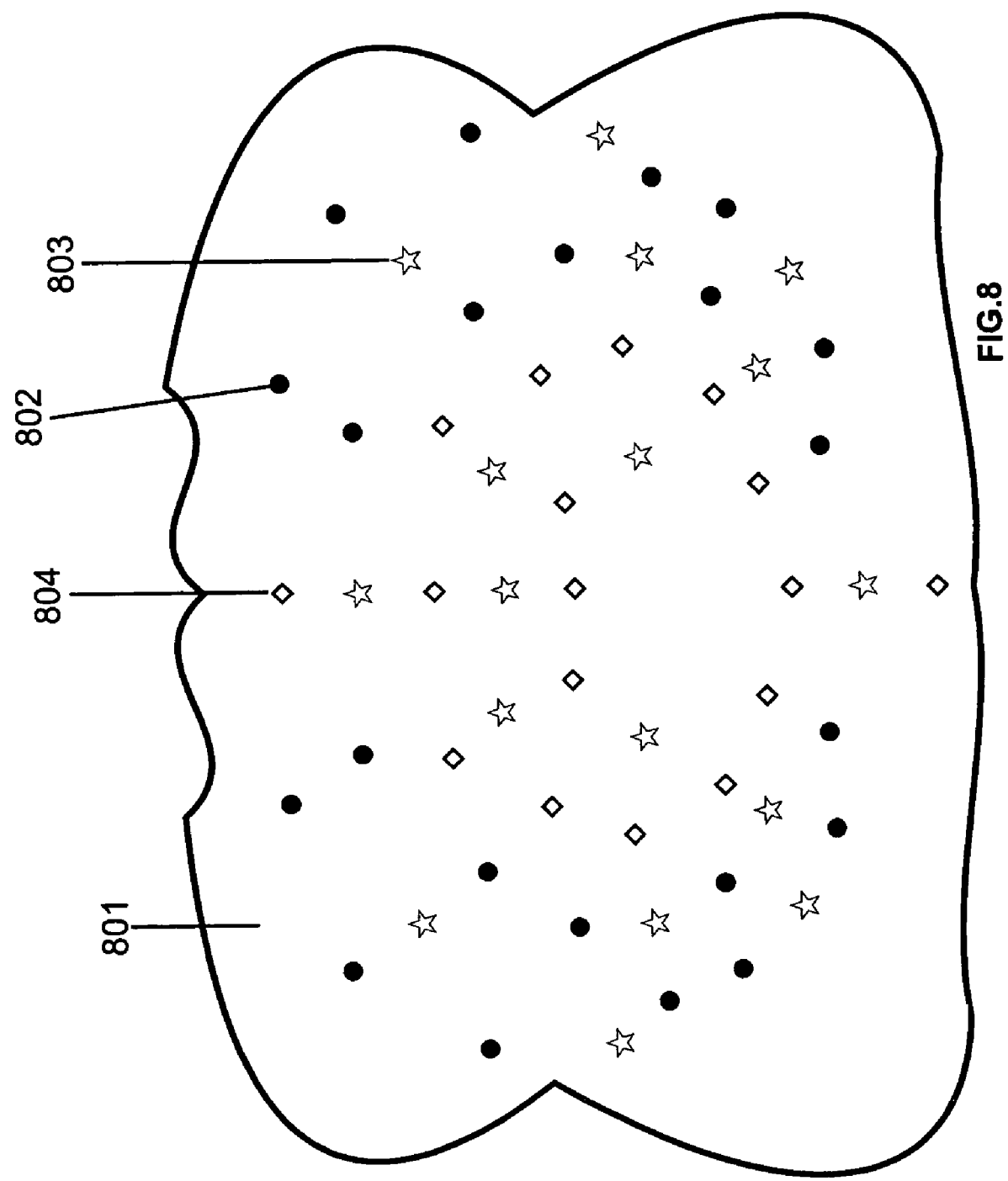
FIG. 8 illustrates a multi-spectra photon therapy pad device wherein the LED array pattern is reflective of anatomical points of interest in the elbow according to one embodiment of the present invention.

Referring now to FIG. 8 a multi-spectra photon therapy elbow pad is illustrated according to one embodiment of the present invention. The multi-spectra photon therapy elbow pad device may include a first set of, e.g., red LEDs illustrated as circles (802) interspersed with at least a second set of, e.g., infrared LEDs illustrated as stars (803) positioned through out the elbow pad. In certain embodiments, the elbow pad may also include a third set of, e.g., infrared LEDs illustrated as diamonds (704) interspersed throughout the first and second set of LEDs. Again, in certain embodiments, the first set of LEDs 502 may emit light in the about red wavelengths, e.g., about 630 nm, the second set of LEDs 503 may emit light in the about infrared wavelengths, e.g., about 760 nm, and the third set of LEDs 504 may emit light in the about infrared wavelengths, e.g., about 880 nm. Other combinations of LEDs are also possible, as described herein. Further, in certain embodiments, the LEDs may be configured in the array in a predetermined pattern reflective of anatomical points of interest in the elbow.

The LEDs of FIG. 8 may be connected to a controller (not shown) through a connector (not shown). The controller contains a timer 150 (FIG. 1.), that controls the on/off duration of the controller, a controller 130 (FIG. 1) that controls the frequency generator 120 (FIG. 1), and an oscillator 110 (FIG. 1) that provides an oscillated signal to the frequency generator 120 (FIG. 1) which provides a modulated signal to the LEDs. A protocol database 170 (FIG. 1) that stores a collection of predetermine frequencies and durations specific to particular conditions or diagnosis. The protocol database 170 (FIG. 1) may optionally be connected to a computer interface 180 (FIG. 1) that allows loading of new protocols as they are needed or developed. The modulated signal is provided to the LED array as illustrated in FIG. 8 whereupon the LED array emits light.

Figure 9:
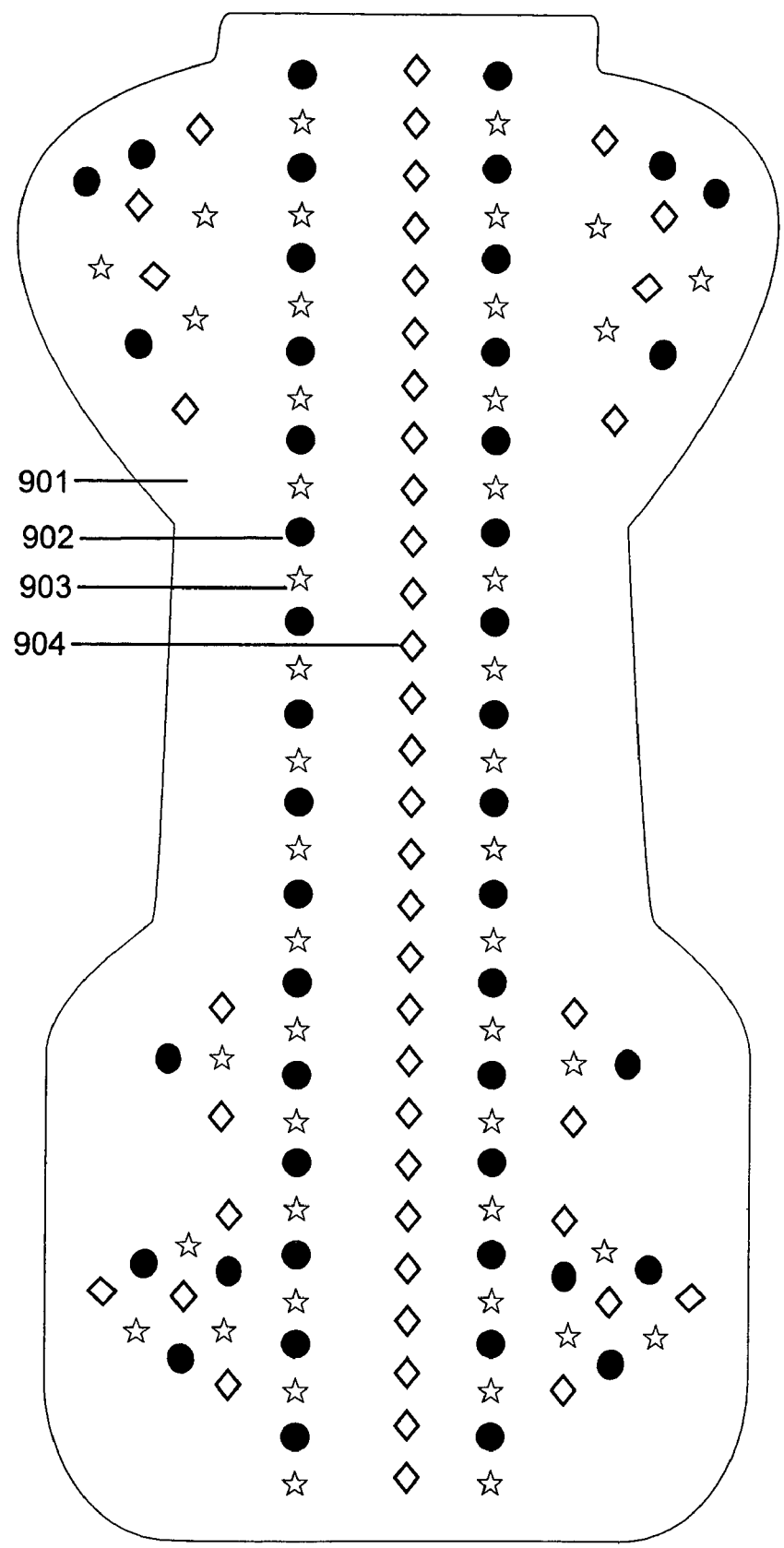
FIG. 9 illustrates a multi-spectra photon therapy pad device wherein the LED array pattern is reflective of anatomical points of interest in the spine (cervical, thoracic, and lumbar regions) according to one embodiment of the present invention.

Referring now to FIG. 9, a multi-spectra photon therapy spinal pad, designed to interface with the cervical, thoracic, and/or lumbar regions of a user, is illustrated according to one embodiment of the present invention. The spinal pad multi-spectra photon therapy device may include a first set of, e.g., red LEDs illustrated as circles (902) interspersed with at least a second set of, e.g., infrared LEDs illustrated as stars (903) positioned through out the spinal pad. In certain embodiments, the spinal pad may also include a third set of, e.g., infrared LEDs illustrated as diamonds (904) interspersed throughout the spinal pad. According to one embodiment of the present invention, the third set of LEDs are positioned along the spine and boney areas, and the second set of LEDs are positioned on either side of the spine. Again, in certain embodiments, the first set of LEDs 902 may emit light in the about red wavelengths, e.g., about 630 nm, the second set of LEDs 903 may emit light in the about infrared wavelengths, e.g., about 760 nm, and the third set of LEDs 904 may emit light in the about infrared wavelengths, e.g., about 880 nm. Other combinations of LEDs are also possible, as described herein. Further, in certain embodiments, the LEDs may be configured in the array in a predetermined pattern reflective of anatomical points of interest in the spine.

The LEDs of FIG. 9 may be connected to a controller (not shown) through a connector (not shown). The controller contains a timer 150 (FIG. 1.), that controls the on/off duration of the controller, a controller 130 (FIG. 1) that controls the frequency generator 120 (FIG. 1), and an oscillator 110 (FIG. 1) that provides an oscillated signal to the frequency generator 120 (FIG. 1) which provides a modulated signal to the LEDs. A protocol database 170 (FIG. 1) that stores a collection of predetermine frequencies and durations specific to particular conditions or diagnosis. The protocol database 170 (FIG. 1) may optionally be connected to a computer interface 180 (FIG. 1) that allows loading of new protocols as they are needed or developed. The modulated signal is provided to the LED array as illustrated in FIG. 9 whereupon the LED array emits light.

Referring now to FIGS. 10A and 10B, a multi-spectra photon therapy lower extremity liner 1001 for use, e.g., with a "boot" device, is illustrated according to one embodiment of the present invention. FIG. 10A shows the liner is front view, as it would wrap the lower extremity of a user. FIG. 10B shows the liner from the top view, as a users foot pad would rest on the bottom surface. The lower extremity multi-spectra photon therapy liner may include a first set of, e.g., red LEDs illustrated as circles (1002) interspersed with at least a second set of, e.g., infrared LEDs illustrated as stars (1003) positioned through out the lower extremity liner. In certain embodiments, the lower extremity liner may also include a third set of, e.g., infrared LEDs illustrated as diamonds (1004) interspersed throughout the first and second set of LEDs. Again, in certain embodiments, the first set of LEDs 1002 may emit light in the about red wavelengths, e.g., about 630 nm, the second set of LEDs 1003 may emit light in the about infrared wavelengths, e.g., about 760 nm, and the third set of LEDs 1004 may emit light in the about infrared wavelengths, e.g., about 880 nm. Other combinations of LEDs are also possible, as described herein. Further, in certain embodiments, the LEDs may be configured in the array in a predetermined pattern reflective of anatomical points of interest in the lower extremity.

The LEDs of FIG. 10 may be connected to a controller (not shown) through a connector (not shown). The controller contains a timer 150 (FIG. 1.), that controls the on/off duration of the controller, a controller 130 (FIG. 1) that controls the frequency generator 120 (FIG. 1), and an oscillator 110 (FIG. 1) that provides an oscillated signal to the frequency generator 120 (FIG. 1) which provides a modulated signal to the LEDs. A protocol database 170 (FIG. 1) that stores a collection of predetermine frequencies and durations specific to particular conditions or diagnosis. The protocol database 170 (FIG. 1) may optionally be connected to a computer interface 180 (FIG. 1) that allows loading of new protocols as they are needed or developed. The modulated signal is provided to the LED array as illustrated in FIG. 10 whereupon the LED array emits light.

Referring now to FIGS. 11A and 11B, the multi-spectra photon therapy lower extremity liner of FIGS. 10A and 10B is illustrated with a lower extremity positioned near the pad according to one embodiment of the present invention. As shown, a user's lower extremity may be placed in the lower extremity liner, with the calf of the user placed against the rear surface 11-1, and the heel of the user placed against the bottom surface 11-2. In certain embodiments, the lower extremity liner may comprise between 150 and 190 LEDs, and more particularly may include about 170 LEDs configured in a predetermined pattern so as to align with specific anatomical sites, as described above. Further, the LEDs may be positioned so as to provide for a variety of viewing angles to thereby accommodate different sizes of users.

Figure 12A:
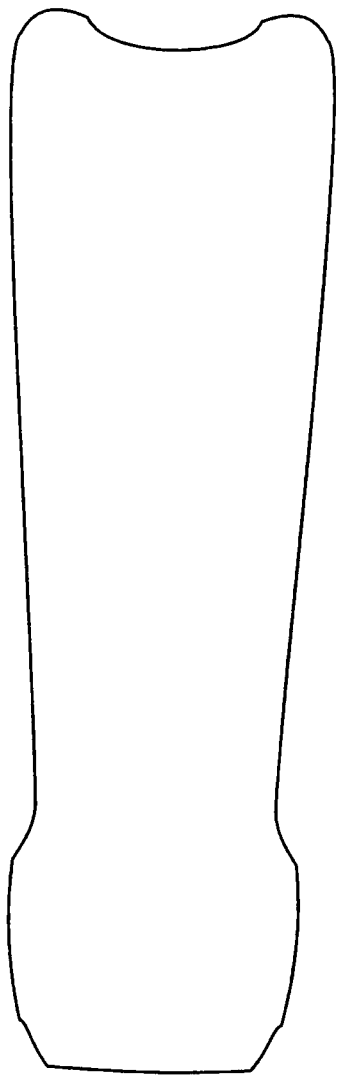
FIGS. 12A, 12B, and 12C illustrates a multi-spectra photon therapy lower extremity boot device according to one embodiment of the present invention.
Figure 12B:
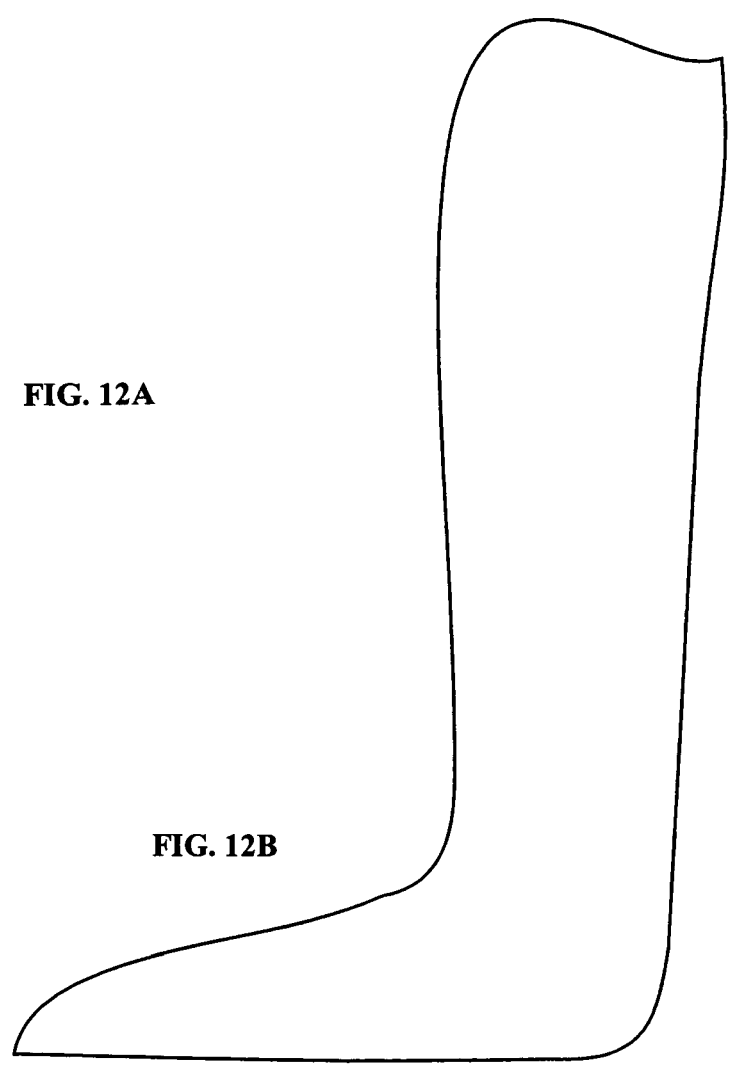
Figure 12C:
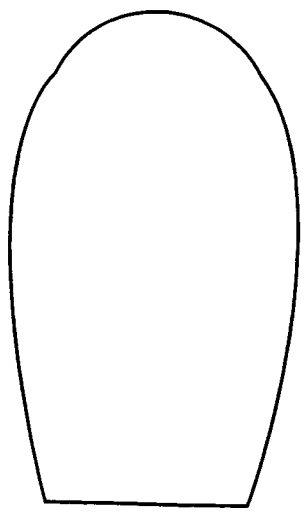
Figure 13A:
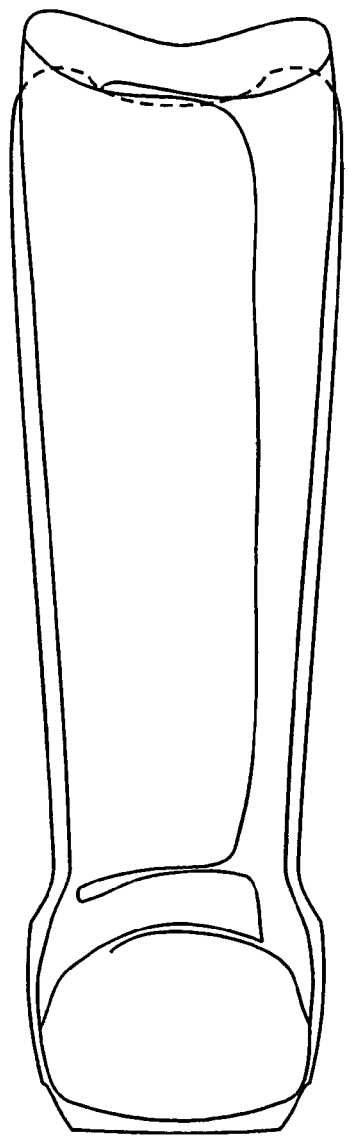
FIGS. 13A and 13B illustrates a multi-spectra photon therapy lower extremity liner of the invention placed inside a boot device according to one embodiment of the present invention.
Figure 13B:
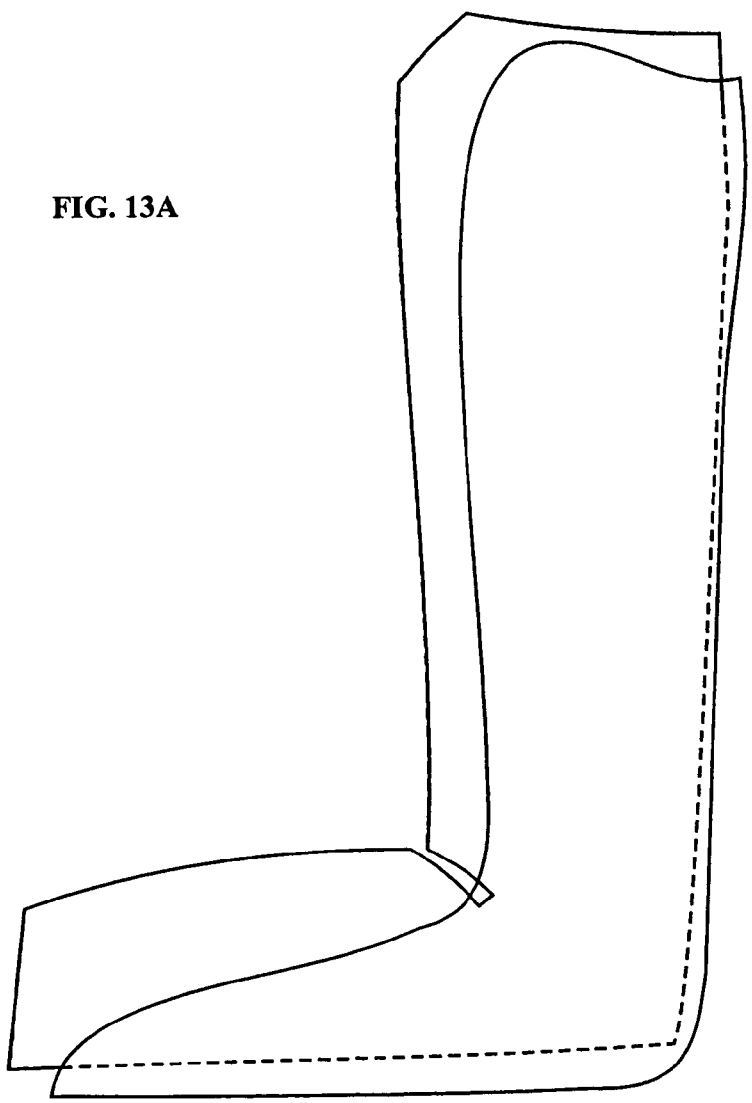

With reference to FIGS. 12A, 12B, and 12C, a multi-spectra photon therapy lower extremity boot shell is illustrated according to another embodiment of the present invention. The boot shell may be used in connection with the liner of FIGS. 10A and 10B as an outer cover to hold the liner in place and protect the liner from damage during use. FIG. 12A shows the boot shell from a front view, FIG. 12B shows the boot shell from a left side view, and FIG. 12C shows the boot shell from a top view. FIGS. 13A and 13B then illustrate the lower extremity liner of FIGS. 10A and 10B placed inside the boot shell of FIGS. 12A, 12B, and 12C.

The multi-spectra photon therapy devices of the invention may alternatively be configured and shaped in any suitable manner so as to interface with desired anatomical locations of a user. For instance, the devices of the invention may be shaped so as to interface with the lower leg, the lower arm, the knee, the ankle, the foot, the toe, the hand, the finger, the wrist, the elbow, the foot, the back, the neck, the head, the eye, the ear, within the mouth, etc., of a user. In certain embodiments, the device of the invention may be shaped as a flexible pad which may be laid against the desired anatomical location, or alternatively may be shaped so as to fit around the desired anatomical location (as exemplified in the above Figures).

Other embodiments of the invention relate to methods of treating or ameliorating a disease or condition which may be affected by MSP light therapy, such as but not limited to those associated with neuropathic pain. The methods of the invention generally comprise positioning a multi-spectra photon therapy device as described above, on or near a subject suffering from a disease or condition of interest, e.g., those associated with neuropathic pain, at an affected anatomical location; and illuminating the anatomical location with the LEDs of the device to thereby treat or ameliorate said disease or condition, e.g., associated with neuropathic pain.

The methods of the invention may be used to treat or ameliorate any suitable disease or condition, including, but not limited to neurological diseases and disorders, such as diabetic peripheral neuropathy, general neuropathy, and carpal tunnel syndrome; chronic pain diseases and disorders, such as arthritis and back pain; orthopedic diseases and disorders, such as joint, bone, and range of motion diseases and disorders; vascular diseases and disorders, such as inflammation and circulation diseases and disorders; soft tissue diseases and disorders, such as tendon, ligament, and muscle disease and disorders; acute injury disease and disorders; wounds; infection; dermatology diseases and disorders, such as acne, hair loss, and pigment disease and disorders; psychological diseases and disorders, such as mood disorders including anxiety and depression; dental diseases and disorders, such as cavitations, pain, edema, and infection; ear diseases and disorders, such as tinnitus, infection, and inflammation; ocular diseases and disorders; and systemic diseases and disorders, such as chronic fatigue syndrome, diabetes and related disorders, and auto-immune diseases and disorders. Again, as described above, in certain embodiments, the LEDs of the device are activated at two or more frequencies in sequence for a predetermined duration of time.

In certain embodiments, the methods of the invention may be used, e.g., to treat or ameliorate symptoms associated with peripheral neuropathy or diabetic peripheral neuropathy. In other embodiments, methods of the invention may be used to treat or ameliorate symptoms associated with neuropathic pain, peripheral neuropathy, diabetic peripheral neuropathy, chronic pain, wound care, infection, arthritis, seasonal affective disorder, headaches, osteoporosis, or inflammation. Any of the methods of the invention may used to treat subjects at anatomical locations, such as, but not limited to the lower leg, the lower arm, the knee, the ankle, the foot, the toe, the hand, the finger, the wrist, the elbow, the foot, the back, the neck, the head, the eye, the ear, within the mouth, etc. Further, the total treatment time may range from about 1 minute to about 45 minutes, from about 5 minutes to about 45 minutes, from about 5 to about 20 minutes, from about 5 to about 15 minutes, from about 7 minutes to about 10 minutes, or about 7, 8, 9, or 10 minutes.

In another aspect of the invention, the MSP therapy devices and methods may be used in connection with combination therapies known in the art for treatment of the specific disease or disorder of interest. By way of non-limiting example, the devices of methods of the invention may be used in connection with acupuncture, acupressure, nutritional support, diathermy, e-stem, gait training, diabetes education, fall prevention, glucose monitoring, exercise, etc. However, any therapy useful in the relevant indication of use may be combined with the MSP therapy devices and methods of the present invention.

EXAMPLES

Examples 1-5

Therapeutic Regimes

In accordance with certain embodiments of the invention, the devices described herein may be configured with the first, second, and third LED sets emitting light in the wavelengths indicated in the table below. Further, the frequency generator may modulate a signal to the LED array, in connection with the control module, at the frequencies indicated for the durations of time indicated.

In certain embodiments, all three sets of LEDs may be illuminated simultaneously at the first frequency for the indicated duration of time, followed by the second, then the third, etc. Alternatively, in other embodiments, the first set of LEDs may be illuminated at the first frequency for the indicated duration of time, then the second set of LEDs may be illuminated at the first frequency for the indicated duration of time, then the third set of LEDs may be illuminated at the first frequency for the indication duration of time, and the sequence may be repeated for the second frequency, and the third frequency, etc. In yet another embodiment, the first set of LEDs may cycle through the entire set of frequencies (i.e., the first frequency for the indicated duration of time, followed by the second frequency, the third frequency, etc.), then the second set of LEDs may cycle through the entire set of frequencies, followed by the third set of LEDs.

| LEDs (nm) | Frequencies (Durations) |
| --- | --- |
| 630/760/880 | 146 Hz (2 minutes), 292 Hz (2 minutes), 584 Hz (2 minutes), 4672 Hz (1 minute) |
| 660/750/890 | 146 Hz (3 min.), 292 Hz (3 minutes), 4672 Hz (1 min.) |
| 630/760/904 | 292 Hz (3 min.), 146 Hz (3 min.), 4672 (1 min.) |
| 630/740/880 | 4672 (1 min.), 146 Hz (2 min.), 292 Hz (2 min.), 584 Hz (2 min), 4672 Hz (30 seconds) |
| 660/760/904 | 292 Hz (2 min.), 146 Hz, (2 min.), 584 Hz, (3 min.) |

Preferred treatment times may vary from about 7 minutes to about 10 minutes, e.g., about 7 minutes, about 8 minutes, about 9 minutes, or about 10 minutes. The treatment time may be adjusted up to 10 minutes by adjusting the individual frequency times by up to 1 minute.

Although the present invention has been described in terms of various exemplary embodiments for purposes of illustration, those of ordinary skill in the art will appreciate that various modifications and improvements may be made to the described embodiments without departing from the scope of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating or ameliorating a disease or condition associated with neuropathic pain using a multi-spectra photon therapy device, said method comprising:

positioning a multi-spectra photon therapy device on or near a subject suffering from a disease or condition associated with neuropathic pain at a predetermined anatomical location;

wherein said multi-spectra photon therapy device comprises an array of light emitting diodes (LEDs) having at least three sets of LEDs, with a first set of LEDs emitting light in the about red wavelengths, and a second set of LEDs emitting light in the about near infrared wavelengths, and at least a third set of LEDs emitting light in the about near infrared wavelengths; and wherein said at least three sets of LEDs are configured according to a predetermined pattern; and illuminating the anatomical location with said at least three sets of LEDs at three or more frequencies, in sequence, in the range of about 0.5 to about 10000 Hz for a predetermined duration of time, to thereby treat or ameliorate said disease or condition associated with neuropathic pain;

wherein the about red wavelengths of said first set of LEDs range from about 630 nm to about 660 nm, and wherein the about near infrared wavelengths of said second and at least third set of LEDs range from about 740 nm to about 905 nm, and wherein said at least three sets of LEDs are activated at sequences of frequencies and durations of time specific to treat or ameliorate a disease or condition associated with neuropathic pain, wherein the frequencies and durations of time are selected from the group consisting of:

about 146 Hz, about 292 Hz, about 584 Hz, and about 4672 Hz, each independently for about 1 second to about 5 minute;

about 146 Hz, about 292 Hz, and about 4672 Hz, each independently for about 1 second to about 5 minute;

about 146 Hz, about 584 Hz, and about 4672Hz, each independently for about 1 second to about 5 minute;

about 146 Hz, about 292 Hz, about 584 Hz, about 292 Hz, and about 584 Hz, each independently for about 1 second to about 5 minute;

about 146 Hz, about 584 Hz, about 1168 Hz, and about 4672 Hz, each independently for about 1 second to about 5 minute;

about 73 Hz, about 584 Hz, about 1168, about 2336 Hz, and about 4672, , each independently for about 1 second to about 5 minute;

about 146 Hz, about 292 Hz, and about 584 Hz, each independently for about 1 second to about 5 minute;

about 292 Hz, about 146 Hz, and about 4672 Hz, each independently for about 1 second to about 5 minute;

about 4672 Hz, about 146 Hz, about 292 Hz, about 584 Hz, and about 4672 Hz, each independently for about 1 second to about 5 minute; and about 292 Hz, about 146 Hz, and about 584 Hz, each independently for about 1 second to about 5 minute.

* * * * *